United States Patent [19]

Bundy

[11] 4,137,403
[45] Jan. 30, 1979

[54] 9-DEOXY-9-METHYLENE-PGF$_2$ CYCLOAMIDES

[75] Inventor: Gordon L. Bundy, Portage, Mich.

[73] Assignee: The Upjohn Company, Kalamazoo, Mich.

[21] Appl. No.: 899,663

[22] Filed: Apr. 24, 1978

Related U.S. Application Data

[63] Continuation-in-part of Ser. No. 786,250, Apr. 11, 1977, Pat. No. 4,098,805.

[51] Int. Cl.$^2$ ............................................. C07C 177/00
[52] U.S. Cl. .................... 542/426; 542/429; 260/326.5 R; 260/326.5 J; 260/239 BC; 544/170; 544/171; 544/172; 544/386; 544/391

[58] Field of Search ............... 542/426, 429; 544/170, 544/171, 172, 386, 391; 260/326.5 R, 326.5 J, 293.8, 293.81, 293.82, 239 BC

[56] References Cited

PUBLICATIONS

Derwent Abstract, 32921w/20, FR 2239458, 31-07-73.
Derwent Abstract, 75530x/40, U.S. 3981868, 14-07-71.

*Primary Examiner*—Paul J. Killos
*Attorney, Agent, or Firm*—Robert A. Armitage

[57] ABSTRACT

The present invention relates to novel 9-deoxy-9-methylene-PGF$_2$ cycloamides. These compounds are useful pharmacological agents, and are useful for the same purposes as the corresponding 9-deoxy-9-methylene-PGF-type acids.

88 Claims, No Drawings

9-DEOXY-9-METHYLENE-PGF₂ CYCLOAMIDES

CROSS REFERENCE TO RELATED APPLICATIONS

This application is a continuation-in-part of Ser. No. 786,250, filed Apr. 11, 1977, now U.S. Pat. No. 4,098,805.

The present invention relates to novel 9-deoxy-9-methylene-PGF₂ cycloamides, the essential material constituting a disclosure of which is incorporated here by reference from Ser. No. 786,250.

I claim:

1. A prostaglandin analog of the formula

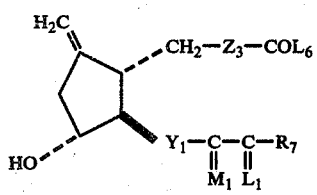

wherein
$Y_1$ is trans—CH=CH—, —C≡C-, or —CH₂CH₂—;
wherein
$M_1$ is

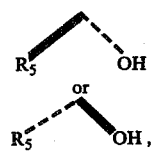

wherein
$R_5$ is hydrogen or methyl;
wherein
$L_2$ is

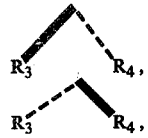

or a mixture of

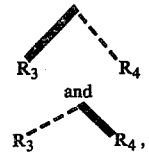

wherein
$R_3$ and $R_4$ are hydrogen, methyl, or fluoro, being the same or different, with the proviso that one of $R_3$ and $R_4$ is fluoro only when the other is hydrogen or fluoro;
wherein
$Z_3$ is
 (1) cis—CH=CH—CH₂—(CH₂)$_g$—CH₂—,
 (2) cis—CH=CH—CH₂—(CH₂)$_g$—CF₂—, or
 (3) cis—CH₂—CH=CH-(CH₂)$_g$—CH₂—,
wherein
g is one, 2, or 3;
wherein
$R_7$ is

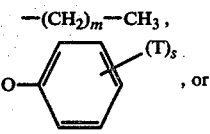

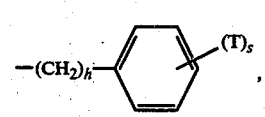

wherein m is one to 5, inclusive, h is zero or one, T is chloro, fluoro, trifluoromethyl, alkyl of one to 3 carbon atoms, inclusive, or alkoxy of one to 3 carbon atoms, inclusive, and s is zero, one, 2, or 3, the various T's being the same or different, with the proviso that not more than two T's are other than alkyl, with the further proviso that $R_7$ is

wherein
T and s are as defined above, only when $R_3$ and $R_4$ are hydrogen or methyl, being the same or different; and
wherein
$L_6$ is cycloamino of the formula

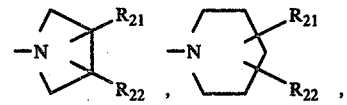

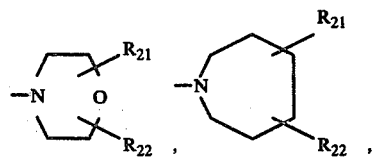

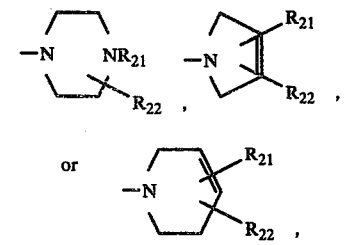

wherein $R_{21}$ and $R_{22}$ are hydrogen, alkyl of one to 12 carbon atoms, inclusive; aralkyl of 7 to 12 carbon atoms, inclusive, phenyl, phenyl substituted with one, 2, or 3 chloro or alkyl of one to 3 carbon atoms, inclusive, or phenyl substituted with hydroxycarbonyl or alkoxycarbonyl of one to 4 carbon atoms, inclusive.

2. A prostaglandin analog according to claim 1, wherein $Y_1$ is —C≡C—.

3. 9-Deoxy-9-methylene-13,14-didehydro-PGF₂, pyrrolidylamide, a prostaglandin analog according to claim 2.

4. 9-Deoxy-9-methylene-13,14-didehydro-PGF$_2$, piperidylamide, a prostaglandin analog according to claim 2.

5. 9-Deoxy-9-methylene-13,14-didehydro-PGF$_2$, morpholinylamide, a prostaglandin analog according to claim 2.

6. 9-Deoxy-9-methylene-13,14-didehydro-PGF$_2$, hexamethyliminoamide, a prostaglandin analog according to claim 2.

7. 9-Deoxy-9-methylene-13,14-didehydro-PGF$_2$, piperazinylamide, a prostaglandin analog according to claim 2.

8. 9-Deoxy-9-methylene-13,14-didehydro-PGF$_2$, 3,4-didehydropyrrolidylamide, a prostaglandin analog according to claim 2.

9. 9-Deoxy-9-methylene-13,14-didehydro-PGF$_2$, 3,4-didehydropiperidylamide, a prostaglandin analog according to claim 2.

10. A prostaglandin analog according to claim 1, wherein Y$_1$ is -CH$_2$CH$_2$-.

11. 9-Deoxy-9-methylene-13,14-dihydro-PGF$_2$, pyrrolidylamide, a prostaglandin analog according to claim 10.

12. 9-Deoxy-9-methylene-13,14-dihydro-PGF$_2$, piperidylamide, a prostaglandin analog according to claim 10.

13. 9-Deoxy-9-methylene-13,14-dihydro-PGF$_2$, morpholinylamide, a prostaglandin analog according to claim 10.

14. 9-Deoxy-9-methylene-13,14-dihydro-PGF$_2$, hexamethyliminoamide, a prostaglandin analog according to claim 10.

15. 9-Deoxy-9-methylene-13,14-dihydro-PGF$_2$, piperazinylamide, a prostaglandin analog according to claim 10.

16. 9-Deoxy-9-methylene-13,14-dihydro-PGF$_2$, 3,4-didehydropyrrolidylamide, a prostaglandin analog according to claim 10.

17. 9-Deoxy-9-methylene-13,14-dihydro-PGF$_2$, 3,4-didehydropiperidylamide, a prostaglandin analog according to claim 10.

18. A prostaglandin analog according to claim 1, wherein Y$_1$ is trans—CH=CH—.

19. A prostaglandin analog according to claim 18, wherein M$_1$ is

20. 15-epi-9-Deoxy-9-methylene-PGF$_2$, pyrrolidylamide, a prostaglandin analog according to claim 19.

21. 15-epi-9-Deoxy-9-methylene-PGF$_2$, piperidylamide, a prostaglandin analog according to claim 19.

22. 15-epi-9-Deoxy-9-methylene-PGF$_2$, morphonylamide, a prostaglandin analog according to claim 19.

23. 15-epi-9-Deoxy-9-methylene-PGF$_2$, hexamethyliminoamide, a prostaglandin analog according to claim 19.

24. 15-epi-9-Deoxy-9-methylene-PGF$_2$, piperazinylamide, a prostaglandin analog according to claim 19.

25. 15-epi-9-Deoxy-9-methylene-PGF$_2$, 3,4-didehydropyrrolidylamide, a prostaglandin analog according to claim 19.

26. 15-epi-9-Deoxy-9-methylene-PGF$_2$, 3,4-didehydropiperidylamide, a prostaglandin analog according to claim 19.

27. A prostaglandin analog according to claim 18, wherein M$_1$ is

28. A prostaglandin analog according to claim 27, wherein Z$_3$ is cis—CH=CH—CH$_2$—(CH$_2$)$_g$—CH$_2$-.

29. A prostaglandin analog according to claim 28, wherein R$_7$ is

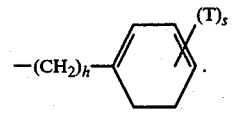

30. 9-Deoxy-9-methylene-17-phenyl-18,19,20-trinor-PGF$_2$, pyrrolidylamide, a prostaglandin analog according to claim 29.

31. 9-Deoxy-9-methylene-17-phenyl-18,19,20-trinor-PGF$_2$, piperidylamide, a prostaglandin analog according to claim 29.

32. 9-Deoxy-9-methylene-17-phenyl-18,19,20-trinor-PGF$_2$, morpholinylamide, a prostaglandin analog according to claim 29.

33. 9-Deoxy-9-methylene-17-phenyl-18,19,20-trinor-PGF$_2$, hexamethyliminoamide, a prostaglandin analog according to claim 29.

34. 9-Deoxy-9-methylene-17-phenyl-18,19,20-trinor-PGF$_2$, piperazinylamide, a prostaglandin analog according to claim 29.

35. 9-Deoxy-9-methylene-17-phenyl-18,19,20-trinor-PGF$_2$, 3,4-didehydropyrrolidylamide, a prostaglandin analog according to claim 29.

36. 9-Deoxy-9-methylene-17-phenyl-18,19,20-trinor-PGF$_2$, 3,4-didehydropiperidylamide, a prostaglandin analog according to claim 29.

37. A prostaglandin analog according to claim 28, wherein R$_7$ is

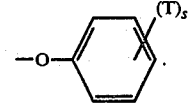

38. 9-Deoxy-9-methylene-16-phenoxy-17,18,19,20-tetranor-PGF$_1$, pyrrolidylamide, a prostaglandin analog according to claim 37.

39. 9-Deoxy-9-methylene-16-phenoxy-17,18,19,20-tetranor-PGF$_1$, piperidylamide, a prostaglandin analog according to claim 37.

40. 9-Deoxy-9-methylene-16-phenoxy-17,18,19,20-tetranor-PGF$_1$, morpholinylamide, a prostaglandin analog according to claim 37.

41. 9-Deoxy-9-methylene-16-phenoxy-17,18,19,20-tetranor-PGF$_1$, hexamethyliminoamide, a prostaglandin analog according to claim 37.

42. 9-Deoxy-9-methylene-16-phenoxy-17,18,19,20-tetranor-PGF$_1$, piperazinylamide, a prostaglandin analog according to claim 37.

43. 9-Deoxy-9-methylene-16-phenoxy-17,18,19,20-tetranor-PGF$_1$, 3,4-didehydropyrrolidylamide, a prostaglandin analog according to claim 37.

44. 9-Deoxy-9-methylene-16-phenoxy-17,18,19,20-tetranor-PGF$_1$, 3,4-didehydropiperidylamide, a prostaglandin analog according to claim 37.

45. A prostaglandin analog according to claim 28, wherein $R_7$ is $-(CH_2)_m-CH_3$.

46. A prostaglandin analog according to claim 45, wherein m is 3.

47. A prostaglandin analog according to claim 46, wherein g is 3.

48. 2a,2b-Dihomo-9-deoxy-9-methylene-15-methyl-PGF$_2$, pyrrolidylamide, a prostaglandin analog according to claim 47.

49. 2a,2b-Dihomo-9-deoxy-9-methylene-15-methyl-PGF$_2$, piperidylamide, a prostaglandin analog according to claim 47.

50. 2a,2b-Dihomo-9-deoxy-9-methylene-15-methyl-PGF$_2$, morpholinylamide, a prostaglandin analog according to claim 47.

51. 2a,2b-Dihomo-9-deoxy-9-methylene-15-methyl-PGF$_2$, hexamethyliminoamide, a prostaglandin analog according to claim 47.

52. 2a,2b-Dihomo-9-deoxy-9-methylene-15-methyl-PGF$_2$, piperazinylamide, a prostaglandin analog according to claim 47.

53. 2a,2b-Dihomo-9-deoxy-9-methylene-15-methyl-PGF$_2$, 3,4-didehydropyrrolidylamide, a prostaglandin analog according to claim 47.

54. 2a,2b-Dihomo-9-deoxy-9-methylene-15-methyl-PGF$_2$, 3,4-didehydropiperidylamide, a prostaglandin analog according to claim 47.

55. A prostaglandin analog according to claim 46, wherein g is one.

56. A prostaglandin analog according to claim 55, wherein at least one of $R_3$ and $R_4$ is methyl.

57. 9-Deoxy-9-methylene-16,16-dimethyl-PGF$_2$, pyrrolidylamide, a prostaglandin analog according to claim 56.

58. 9-Deoxy-9-methylene-16,16-dimethyl-PGF$_2$, piperidylamide, a prostaglandin analog according to claim 56.

59. 9-Deoxy-9-methylene-16,16-dimethyl-PGF$_2$, morpholinylamide, a prostaglandin analog according to claim 56.

60. 9-Deoxy-9-methylene-16,16-dimethyl-PGF$_2$, hexamethyliminoamide, a prostaglandin analog according to claim 56.

61. 9-Deoxy-9-methylene-16,16-dimethyl-PGF$_2$, piperazinylamide, a prostaglandin analog according to claim 56.

62. 9-Deoxy-9-methylene-16,16-dimethyl-PGF$_2$, 3,4-didehydropyrrolidylamide, a prostaglandin analog according to claim 56.

63. 9-Deoxy-9-methylene-16,16-dimethyl-PGF$_2$, 3,4-didehydropiperadylamide, a prostaglandin analog according to claim 56.

64. A prostaglandin analog according to claim 55, wherein at least one of $R_3$ and $R_4$ is fluoro.

65. 9-Deoxy-9-methylene-16,16-difluoro-PGF$_2$, pyrrolidylamide, a prostaglandin analog according to claim 64.

66. 9-Deoxy-9-methylene-16,16-difluoro-PGF$_2$, piperidylamide, a prostaglandin analog according to claim 64.

67. 9-Deoxy-9-methylene-16,16-difluoro-PGF$_2$, morpholinylamide, a prostaglandin analog according to claim 64.

68. 9-Deoxy-9-methylene-16,16-difluoro-PGF$_2$, hexamethyliminoamide, a prostaglandin analog according to claim 64.

69. 9-Deoxy-9-methylene-16,16-difluoro-PGF$_2$, piperazinylamide, a prostaglandin analog according to claim 64.

70. 9-Deoxy-9-methylene-16,16-difluoro-PGF$_2$, 3,4-didehydropyrrolidylamide, a prostaglandin analog according to claim 64.

71. 9-Deoxy-9-methylene-16,16-difluoro-PGF$_2$, 3,4-didehydropiperadylamide, a prostaglandin analog according to claim 64.

72. A prostaglandin analog according to claim 55, wherein $R_3$ and $R_4$ are both hydrogen.

73. A prostaglandin analog according to claim 72, wherein $R_5$ is methyl.

74. 9-Deoxy-9-methylene-15-methyl-PGF$_2$, pyrrolidylamide, a prostaglandin analog according to claim 73.

75. 9-Deoxy-9-methylene-15-methyl-PGF$_2$, piperidylamide, a prostaglandin analog according to claim 73.

76. 9-Deoxy-9-methylene-15-methyl-PGF$_2$, morpholinylamide, a prostaglandin analog according to claim 73.

77. 9-Deoxy-9-methylene-15-methyl-PGF$_2$, hexamethyliminoamide, a prostaglandin analog according to claim 73.

78. 9-Deoxy-9-methylene-15-methyl-PGF$_2$, piperazinylamide, a prostaglandin analog according to claim 73.

79. 9-Deoxy-9-methylene-15-methyl-PGF$_2$, 3,4-didehydropyrrolidylamide, a prostaglandin analog according to claim 73.

80. 9-Deoxy-9-methylene-15-methyl-PGF$_2$, 3,4-didehydropiperadylamide, a prostaglandin analog according to claim 73.

81. A prostaglandin analog according to claim 72, wherein $R_5$ is hydrogen.

82. 9-Deoxy-9-methylene-PGF$_2$, pyrrolidylamide, a prostaglandin analog according to claim 81.

83. 9-Deoxy-9-methylene-PGF$_2$, piperidylamide, a prostaglandin analog according to claim 81.

84. 9-Deoxy-9-methylene-PGF$_2$, morpholinylamide, a prostaglandin analog according to claim 81.

85. 9-Deoxy-9-methylene-PGF$_2$, hexamethyliminoamide, a prostaglandin analog according to claim 81.

86. 9-Deoxy-9-methylene-PGF$_2$, piperazinylamide, a prostaglandin analog according to claim 81.

87. 9-Deoxy-9-methylene-PGF$_2$, 3,4-didehydropyrrolidylamide, a prostaglandin analog according to claim 81.

88. 9-Deoxy-9-methylene-PGF$_2$, 3,4-didehydropiperazinylamide, a prostaglandin analog according to claim 81.

* * * * *

UNITED STATES PATENT AND TRADEMARK OFFICE
CERTIFICATE OF CORRECTION

PATENT NO. : 4,137,403
DATED : January 30, 1979
INVENTOR(S) : Gordon L. Bundy

It is certified that error appears in the above-identified patent and that said Letters Patent are hereby corrected as shown below:

Column 4, lines 49, 52, 55, 58, 61, 64, and 67, "$PGF_1$" should read -- $PGF_2$ --;

Column 6, line 17, "didehydropiperadylamide," should read -- didehydropiperidylamide, --.

Signed and Sealed this

Twelfth Day of June 1979

[SEAL]

Attest:

RUTH C. MASON
Attesting Officer

DONALD W. BANNER
Commissioner of Patents and Trademarks